(12) United States Patent
Gomez et al.

(10) Patent No.: US 11,730,914 B2
(45) Date of Patent: Aug. 22, 2023

(54) APPARATUS AND METHOD FOR LOCATING A NERVE BLOCK SITE BY ESTABLISHING A REFERENCE PLANE AND DELIVERING ANESTHETIC TO THE SITE

(71) Applicant: New Wave Endo-Surgery Inc., Coconut Creek, FL (US)

(72) Inventors: Ricardo Alexander Gomez, Light House, FL (US); Sandy Lawrence Heck, Los Angeles, CA (US); Eric William Conley, South Berwick, ME (US); Luis David Suazo, Tamarac, FL (US)

(73) Assignee: New Wave Endo-Surgical Corp., Coconut Creek, FL (US)

( * ) Notice: Subject to any disclaimer, the term of this patent is extended or adjusted under 35 U.S.C. 154(b) by 852 days.

(21) Appl. No.: 16/437,463

(22) Filed: Jun. 11, 2019

(65) Prior Publication Data
US 2019/0374729 A1 Dec. 12, 2019

Related U.S. Application Data

(60) Provisional application No. 62/683,129, filed on Jun. 11, 2018.

(51) Int. Cl.
*A61M 19/00* (2006.01)
*A61M 5/48* (2006.01)
*A61M 5/46* (2006.01)

(52) U.S. Cl.
CPC ............ *A61M 19/00* (2013.01); *A61M 5/46* (2013.01); *A61M 5/486* (2013.01)

(58) Field of Classification Search
CPC . A61M 19/00; A61M 5/46; A61B 2017/3407; A61B 2017/3405
See application file for complete search history.

(56) References Cited

U.S. PATENT DOCUMENTS

| 2011/0201930 | A1 | 8/2011 | Guzman |
| 2014/0025039 | A1* | 1/2014 | Rajendran ............ A61M 19/00 604/512 |
| 2015/0038997 | A1* | 2/2015 | Malkowski ........ A61B 17/3417 606/148 |
| 2016/0136381 | A1 | 5/2016 | Guzman |
| 2017/0165450 | A1 | 6/2017 | Guzman |

FOREIGN PATENT DOCUMENTS

WO 2017178817 A1 10/2017

OTHER PUBLICATIONS

International Search Report dated Sep. 3, 2019 From Corresponding Application No. PCT/US2019/036531 Filed on Jun. 11, 2019.

\* cited by examiner

*Primary Examiner* — Emily L Schmidt
(74) *Attorney, Agent, or Firm* — Grogan, Tuccillo & Vanderleeden LLP

(57) ABSTRACT

The present disclosure relates to a local anesthetic delivery device for delivering anesthetic to a nerve block site comprising a surgical mechanism for establishing a reference plane for identifying the nerve block site, wherein the surgical mechanism establishes the reference plane at the peritoneum and uses a known fixed distance to the nerve plane above to accurately locate the nerve block site and deliver anesthesia.

10 Claims, 6 Drawing Sheets

APPARATUS AND METHOD FOR LOCATING A NERVE BLOCK SITE BY ESTABLISHING A REFERENCE PLANE AND DELIVERING ANESTHETIC TO THE SITE

CROSS-REFERENCE TO RELATED APPLICATIONS DISCLOSURE

The application claims the benefit of U.S. Provisional Patent Application No. 62/683,129 filed Jun. 11, 2018, entitled "Port Site Injector for Establishing a Reference Plane and Delivering Local Anesthetic Block After Laparoscopic Procedures", which is hereby incorporated by reference in its entirety as if fully restated herein.

FIELD

The present field of disclosure relates generally to the field of laparoscopic and minimally invasive surgery. More specifically to an apparatus and method for locating a nerve block site by establishing a reference plane using the peritoneum as the fixed reference point.

BACKGROUND

The Transversus Abdominis Plane (TAP) and Rectus Sheath (RS) blocks are effective methods of providing analgesia in patients undergoing abdominal surgery. Procedures called a TAP block and RS block are the standard techniques used to deliver anesthetic to a localized area inside the abdominal wall. The aim of the TAP and RS block is to deposit a large volume of local anesthetic into the space where the nerves travel: a nerve plane. The concentration of anesthetic solution used depends on the calculated maximum dose of local anesthetic allowed. The technique anesthetizes the nerves in those regions and effectively reduces pain associated with abdominal incisions in surgeries. An important component of the pain patients experience after abdominal surgery derives from the abdominal wall incision. This often requires patients to receive opioids after surgery to deal with the pain, which introduces significant risk and morbidity associated with opiate use, including dangerous side effects and possibly addiction The lateral abdominal wall consists of three muscle layers separated by thin planes. The first muscle layer closest to exterior is called the external oblique muscle, in the middle are the internal oblique muscle, and inferiorly the transversus abdominus muscle. In between the internal oblique muscle and the transversus abdominus is with a space, or plane, containing nerves responsible for pain. This area is called the Transversus Abdominus Plane. By introducing local anesthetics into the TAP, it is possible to block the sensory nerves of the anterior abdominal wall. In the anterior abdominal wall, there is a plane of nerves that travel in the rectus sheath, a space similar to the TAP but between the abdominus rectus muscle and the peritoneum.

The known techniques locate the nerves by using an imaging device e.g., an ultrasound, to track the insertion of a needle containing anesthetic into a nerve plane. The needle is inserted into an abdominal wall through the epidermis and is guided inward towards the nerve plane, and a fixed point for determining the depth of the nerve plane inside the abdominal wall is the epidermis or another layer of tissue inside the abdominal wall that is outwardly located when compared to the nerve plane. The know techniques are imprecise and can result in requiring multiple attempts to correctly place the needle in the nerve plane. There remains a need for an apparatus and a method that precisely places a needle that introduces an analgesic into a nerve plane without requiring ultrasound visualization or imprecise techniques.

SUMMARY

Recent studies have shown that if surgeons inject anesthesia in the deep layer of the abdominal wall at the end of a surgical procedure, it can lead to significant reduction in pain and reduced opioid consumption post-op. The problem surgeons are encountering today is that it is difficult to target this nerve layer as there is a significant variation between people in the distance between the skin and the nerve layer which is deep inside the abdominal wall. Different people have different thickness of skin, varying fat layer, and muscle thickness that can all vary up to 70 mm between individuals. Currently the only way to accurately target this area is by using an ultrasound machine and viewing the needle as it penetrates the tissue until the doctor visualizes the needle reaching the deep nerve layer. This is the preferred method today, but the size of the ultrasound equipment, the added costs, and the delays make it impractical to do at the end of surgery. It is even more so for smaller surgical procedures like laparoscopy or robotic surgery, and the cumbersomeness of this equipment is a significant reason abdominal nerve blocks are rarely used in these minimally invasive procedures. Some surgeons have resorted to performing it blindly and trying to tactilely feel the needle penetrating the different layers, but these blind methods have been proven in studies to be inaccurate and dangerous as the needle could surpass the nerve layer and enter the abdomen or injure the intra-abdominal organs.

This disclosure has the potential to reduce opiate use and improve patient satisfaction by eliminating pain in a safe, easy and affordable manner. The lateral abdominal wall consists of three muscle layers separated by thin planes. The first muscle layer closest to exterior is called the external oblique muscle, in the middle are the internal oblique muscle, and inferiorly the transversus abdominus muscle. In between the internal oblique muscle and the transversus abdominus is with a space, or plane, containing nerves responsible for pain. This area is called the Transversus Abdominus Plane. By introducing local anesthetics into the TAP, it is possible to block the sensory nerves of the anterior abdominal wall. In the anterior abdominal wall, there is a plane of nerves that travel in the rectus sheath, a space similar to the TAP but between the abdominus rectus muscle and the fascia.

The precise placing of the needle that introduces an analgesic into these spaces is vital for pain reduction. Procedures called a TAP block and RS block are used to achieve this goal. The aim of the TAP and RS block is to deposit a large volume of local anesthetic into the space where the nerves travel. The concentration of solution used will depend on the calculated maximum dose of local anesthetic allowed.

An independent study performed on over 100 randomly selected individuals of different ages, sexes and body sizes determined that there is a very consistent relationship in the distance between an anatomical structure at the bottom of the abdomen called the peritoneum and the location of the nerve layer above it that needs to be targeted. The distance from the skin to the nerve layer varies dramatically between individuals, because, in part, the fat and muscle layers on each individual are different thicknesses. It was found that if one uses the peritoneum as the fixed point for locating the nerve layer, then one can target the nerve layer consistently. This special anatomical relationship of the peritoneum and the nerve layer can be utilized using a tool that uses the peritoneum as a reference to then consistently deliver a needle to the nerve layer above it without ultrasound and without guesswork. The device uses the peritoneum as a reference to then provide a hard stop that physically stops the needle and delivers the tip anywhere from 0.1 cm to 1 cm above the reference so that the injection has a very high likelihood that it will enter the correct nerve layer regardless of the individual's shape, size, age, or sex.

By studying normal individuals of varying size, age, and sex, a unique relationship between the two independent anatomical structures was identified showing minimal variation from individual to individual. Dispersing analgesic between 0.1 cm and 1 cm above the peritoneum will block the sensory nerves that run along the deep abdominal nerve plane that would otherwise, prior to this disclosure, require ultrasound equipment to precisely locate.

One embodiment of this disclosure provides a means for quickly and accurately finding the sensory nerves using a mechanical device and using the peritoneum as the reference point or fixed point.

The present disclosure provides a method and apparatus for reaching a nerve plane, such as the TAP and RS, and then applying an anesthetic block to the nerve plane. The anesthetic block can be applied before or after laparoscopic surgery. In the depictions of this application, several examples of injector devices are shown, and are not to be considered as limiting for the injector device. Also shown are different novel approaches for introducing an analgesic substance.

Currently, properly performing a TAP or RS block requires coordinating with an anesthesiologist to use ultrasound guidance to place the needle and inject the anesthesia into the appropriate area. Care must be given when performing these procedures, because placing the needle too far inward can result in injury to intra-abdominal organs, while not inserting the needle far enough inward can result in the anesthesia missing the target nerves and not anesthetizing the desired area. Surgeons have adopted several techniques to attempt these blocks without the delays and added costs associated with using ultrasound. Such techniques, which include using anatomic landmarks and feeling for the sensation of the needle as it passes through each abdominal layer, are often inaccurate and expose the patient to added risk of complications from the procedure In one embodiment of the present disclosure, a local anesthetic delivery device can comprise a specialized surgical needle having a proximal end and a distal end, a grip handler located at the proximal end, a needle tip located at the distal end, and an inner cannula, wherein the inner cannula traverses an entire length of the specialized surgical needle and is capable of advancing an anesthetic from said proximal end of said specialized surgical needle toward said distal end of said specialized surgical needle, and the needle tip having multiple circular openings pre-configured to reach and deliver anesthesia to a nerve block site.

In another embodiment of the present disclosure, a trocar device is inserted into the coelom through an incision, and through the peritoneum. Once the trocar device enters the peritoneal space inward of the outer peritoneum layer (parietal peritoneum), it is pulled outwards (or upwards, if the patient is lying horizontal on an operating table), and at least one tubular stop tab that the distal end of the trocar rotate from being orientated in a parallel position with the sides of the trocar to being orientated in a horizontal position with the sides of the trocar.

In another embodiment of the present disclosure, a curved inverse needle can be used. The curved inverse needle is inserted into a trocar device, which is inserted into the body through an incision, and through the peritoneum. The curved inverse needle can be pushed to the edge of trocar and pulled upwards so its inverted tip re-enters through the parietal cavity, into the peritoneum, and terminates at the precise location of the targeted plane or nerve plane or targeted nerve plane. The needle may have a single distal opening or may have one or more holes along its distal length. This unique approach is unlike any currently used in the industry.

In another embodiment of the present disclosure, another specialized needle device is inserted diagonally through a canula device, or trocar, with the trocar providing a reference plane in a fixed location against the peritoneum. This can be achieved with at least one wing, tab, or tubular stop tab that restricts the trocar from sliding out of place when pulled upwards. With the trocar in a fixed location relative to the peritoneum, features in the trocar can stop the needle at a specific distance from the peritoneum, thereby allowing for the needle to terminate or penetrate into the correct plane.

In another embodiment of the present disclosure, a specialized needle device is seen inserted into an abdomen, either directly through the skin or through an already established port. The tip of the specialized needle is flexible which permits it to change its angle and provide a unique approach to the transversus abdominus plane. The needle has a feature that provides resistance at a predetermined insertion length, thereby providing a reference plane for measuring the distance to the correct nerve plan location, such as in a TAP or RS block locations. This can be achieved by incorporating a widened segment of the needle that only permits a predetermined length of distal thin needle to enter the peritoneum before resistance is encountered. Most TAP blocks are inserted from the top skin layer or epidermis and are guided inward into the body, through the layers of the abdomen, and into the nerve block site. The present disclosure describes a novel approach where the block is performed from the interior of the abdominal cavity outwards. The end of the needle or needle tip may also incorporate multiple symmetric opening for accessing the transversus abdominus plane.

In another embodiment of the present disclosure, specialized guide needles are used with multiple symmetric openings for reaching the transversus abdominus plane and the rectus sheath sensory nerves. This approach permits an analgesic to dispose out of the symmetric openings that are prepositioned to where the transversus abdominus plane is located. Correctly placing a needle or needle tip into the Transversus Abdominus Plane (TAP) or Rectus Sheath (RS), by means of predetermining the correct distance to the Transverse Abdominus Plane from the peritoneum and using multiple openings on the needle surface to disburse the anesthetic. The nerve plane can be reached by the needle tip from the peritoneum upwards or outwards to a predetermined distance.

In another embodiment of the present disclosure, specialized injector needles may have a distal opening as well as a row of fenestrations along the distal segment of the needle. The openings can be in a single row or be symmetrically placed along the segment. These small holes on the needle permit the needle to disperse an analgesic into a broader space, which has several benefits. The variation in abdominal wall thickness from one person or individual to the next and can be considerable, but most of this variation is due to the layers of fat in the anterior wall. The posterior abdominal wall is far less variable, allowing for consistency from one patient to the next, however there is still some variability. Allowing the anesthetic to exit the needle in a range of distances, rather than a single spot, helps ensure that the correct plane is hit in every patient. Additionally, the targeted plane is anatomically the plane with least resistance, so when anesthetic is pushed out under pressure, it will naturally disperse into the correct plane as long as the plane is within the range of holes. Local infiltration (anesthetic broadly injected into the areas of the incision, rather than specifically placed in a nerve plane) has pain control benefits, and an injector that can deliver anesthesia to the correct plane and to the local region can aid in reducing the amount of opioid prescribed to the individual to manage the pain caused by the procedure. In one embodiment, the row of fenestrations is placed on the side of the needle oriented away from the trocar. Since the placement of a trocar through the fascial skin layer creates an opening into the abdominal cavity, it is beneficial to have the anesthetic injected away from the trocar hole, so that it can be efficiently distributed to the tissues, rather than towards the trocar hole where some amount may be lost into the abdomen.

Although one embodiment incorporates a physical mechanism to establish the reference plane against the interior abdominal wall, other methods for establishing the reference plane can be incorporated into the needle. In one embodiment, (not shown) the needle incorporates a removable internal light source within its inner cannula. As the laparoscopic surgeon watches from the inside of the abdomen cavity, the light would illuminate the transversus abdominus fascia when the needle has progressed to the correct depth, thereby correctly identifying the reference plane and signaling to the surgeon that the needle tip is in the correct location. Similarly, in an alternative embodiment, the needle incorporates a removable ultrasonic probe within its inner cannula. When the probe detects the thicker fascial layer, it has identified the reference plane and indicates to the surgeon that the needle tip is in the correct location relative to the reference plane. Alternatively, the ultrasound probe can instead be a pressure sensor which identifies the changes of pressure as the needle progresses through the various layers of skin, fat, muscle and connective tissue in the abdominal wall. When the needle has identified the reference plane by characterizing the pressure changes consistent with that layer, the surgeon can safely inject the anesthetic.

The needles disclosed herein can be made from, but are not limited to, stainless steel, nitinol, or any material commonly used in the industry. The needle systems that fit through trocars can be sized for any 5-12 mm trocar. The use of a reference plane, as well as the use of multi-fenestrated needle tips can be incorporated into any of the needles described above as stand-alone devices, or in combination with any device used to deliver anesthesia into the desired nerve plane, such as the RS and TAP space. Including a specialized trocar comprising pre-determined specialized passages that lie along the TAP (Transversus Abdominal Plane) or RS (Rectus Sheath) to provide an analgesic path.

The relationship between the two anatomical planes of the peritoneum and the nerve plane, such as the rectus sheath establish the reference plane used to precisely and reliably deliver anesthetic to the nerve plane.

These and other aspects and features of the present disclosure will become more readily apparent from the attached drawings and the detailed description of the preferred embodiments, which follow. This Summary is not to be construed as limiting.

BRIEF DESCRIPTION OF THE DRAWINGS

The preferred embodiments of the disclosure will hereinafter be described in conjunction with the appended drawings provided to illustrate and not to limit the disclosure, in which.

Like reference numerals refer to like parts throughout the several views of the drawings.

DETAILED DESCRIPTION

Figure 1:
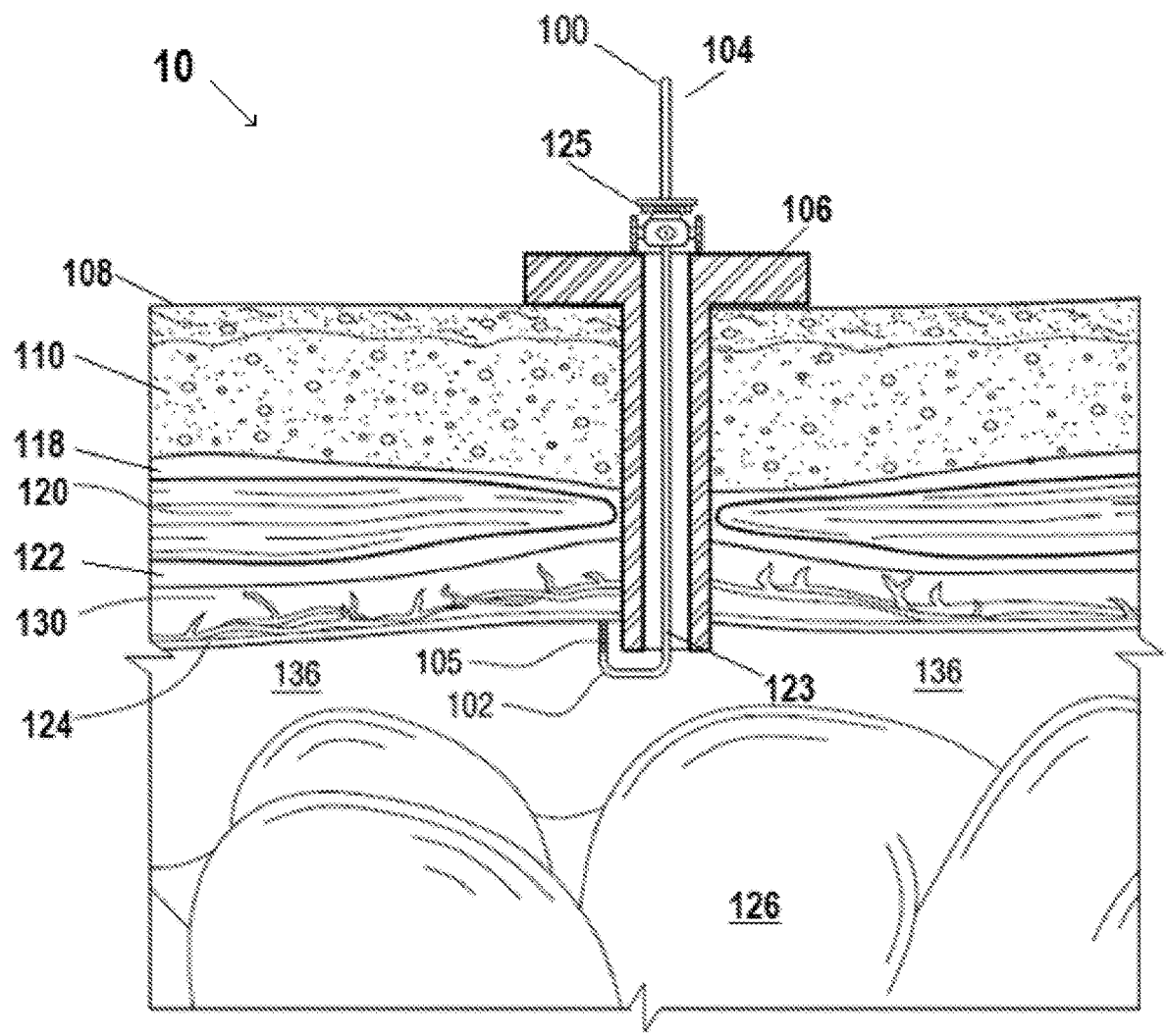
FIG. 1 shows a perspective view of one embodiment of a local anesthetic delivery device of the present disclosure and illustrates a specialized inverted surgical needle pre-deployed.

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper", "lower", "left", "rear", "right", "front", "vertical", "horizontal", and derivatives thereof shall relate to the disclosure as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Generally, the present disclosure teaches a local anesthetic delivery device for delivering anesthetic to a nerve block site comprising a surgical mechanism for establishing a reference plane for identifying the nerve block site, wherein the surgical mechanism establishes the reference plane at the peritoneum and uses a fixed distance to a nerve plane for locating the nerve block site and positioning the needle.

The local anesthetic delivery can further comprise a specialized surgical needle having a proximal end and a distal end, a grip handler located at the proximal end, a needle tip located at the distal end, and an inner cannula, wherein the inner cannula traverses an entire length of the specialized surgical needle and is capable of advancing an anesthetic from said proximal end of said specialized surgical needle toward said distal end of said specialized surgical needle, and the needle tip having multiple circular openings pre-configured to reach and deliver anesthesia to a nerve block site.

The surgical mechanism establishes the reference plane by measuring the distance from the parietal peritoneum outwards to the nerve block site. The distance from the peritoneum outwards to the nerve block site can be 0.1 cm to 1 cm, and the surgical mechanism can comprise a physical mechanism, a removable ultrasonic probe incorporated in the inner cannula of the specialized surgical needle, or a removable internal light source incorporated in inner cannula of the specialized surgical needle. Further, the multiple circular openings can be miniature openings.

The local anesthetic delivery device can further comprise a trocar that establishes a reference plane with a tubular stop tab at a distal end of the trocar. The trocar can comprise a guide ring wherein the guide ring orients and positions the specialized surgical needle to reach the nerve block site. The nerve block site can be a transversus abdominus plane, rectus sheath, or another nerve plane, to which the needle would be directed relative to the reference plane established by the trocar's distal stop tabs.

In general, the present disclosure teaches a method for delivering a nerve block by establishing a reference plane for identifying the nerve block site, wherein the reference plane is established by creating a stop feature positioned against the peritoneum as a fixed point for measuring a distance to the nerve plane. Said local anesthetic delivery device is guided into the abdominal wall from the outside of a body, positioning the local anesthetic delivery device in the nerve block site that was identified relative to the reference plane, and delivering anesthesia into the nerve plane through multiple openings along the tip of the local anesthetic delivery device.

The method can use various methods for establishing the reference plane. The mechanism can be a physical mechanism incorporated into the device, a removable ultrasonic probe incorporated in an inner cannula of the device, or a removable internal light source incorporated into the device. The surgical mechanism for establishing a reference plane can also be an incorporated into a trocar. A broad area of the nerve block site can be coated with anesthesia through miniature openings located at the distal end of the anesthetic delivery device. Pulling the trocar upward after insertion engages the at least one tubular stop tab located at the distal end of the trocar to stop the trocar from moving further inward into the coelom after the distal end has passed through the peritoneum and into the intraperitoneal space.

Anesthesia can be delivered to the nerve block site in the nerve plane through multiple openings the tip of the local anesthetic delivery device. The reference plane for identifying a nerve block site can be established by locating the nerve plane using a peritoneum as a fixed point for determining a distance to the nerve plane.

Turning now to the Figures, FIG. 1 illustrates one embodiment of a local anesthetic delivery device (10). A specialized surgical needle (100) is depicted going through a trocar device (106). The trocar device (106) comprises side walls has been inserted into the abdominal cavity (136) or coelom by making an incision that extends inward into the abdominal cavity (136) from the epidermis through the peritoneum (124). The trocar device (106) is used to insert and remove laparoscopic instruments during the procedure. The specialized surgical needle (100) has a curved end (102) that is designed to remain rigid and a needle tip having multiple circular openings (105) pre-configured to reach the nerve plane or sensory nerve plane (130), with the curved segment effectively creating the reference plane at the peritoneum (124). The needle rises a fixed distance relative to the peritoneum, and is thereby positioned in the nerve plane. The multiple circular openings near the needle tip (105) provide a means of distributing an analgesic substance to the sensory nerves (130). The specialized needle is guided to the correct distance in the sensory nerve plane (130) by the distance guide controller (125). As the guide controller (125) is spun it controls the movement of the specialized needle body (123). The device can also be operated without a guide controller (125), and can be pulled upwards manually until resistance is felt and the curved part of the needle is pressed up against the peritoneum. Unlike other methods and devices used for applying an abdominal wall nerve block, this embodiment utilizes the distance relationship between the peritoneum and the sensory nerve plane. The specialized surgical needle (100), such as an inverted specialized surgical needle, does not have to be exactly at the Rectus Sheath Plane in order to be effective. The length of the specialized surgical needle (100) can be adjusted to effectively reach the sensory nerve (130) plane by the distance guide controller (125). The specialized surgical needle (100) is designed so as not to injure, pierce, or otherwise harm the intestines (126) or other abdominal organs once it enters the abdominal cavity (136). The distance guide controller (125) controls the distance the specialized surgical needle (100) will travel once it is inside the body. The sensory nerve plane (130) can be located at 0.1 cm to 1 cm, or at any distance within that range, upward or outward of the peritoneum (124) towards the epidermis (108). More particularly, the sensory nerve plane (130) can be located at 0.1 cm to 0.9 cm, 0.1. to 0.8 cm, 0.1 cm to 0.7 cm, 0.1 cm to 0.6 cm, 0.1 to 0.5 cm, 0.1 to 0.4 cm, 0.1 cm to 0.3 cm, 0.2 cm to 1 cm, 0.2 cm to 0.9 cm, 0.2 cm to 0.8 cm, 0.2 cm to 0.7 cm, 0.2 cm to 0.6 cm, 0.2 cm to 0.5 cm, 0.2 to 0.4 cm, or at 0.2 to 0.3 cm upward or outward of the peritoneum (124) towards the epidermis (108).

Figure 2:
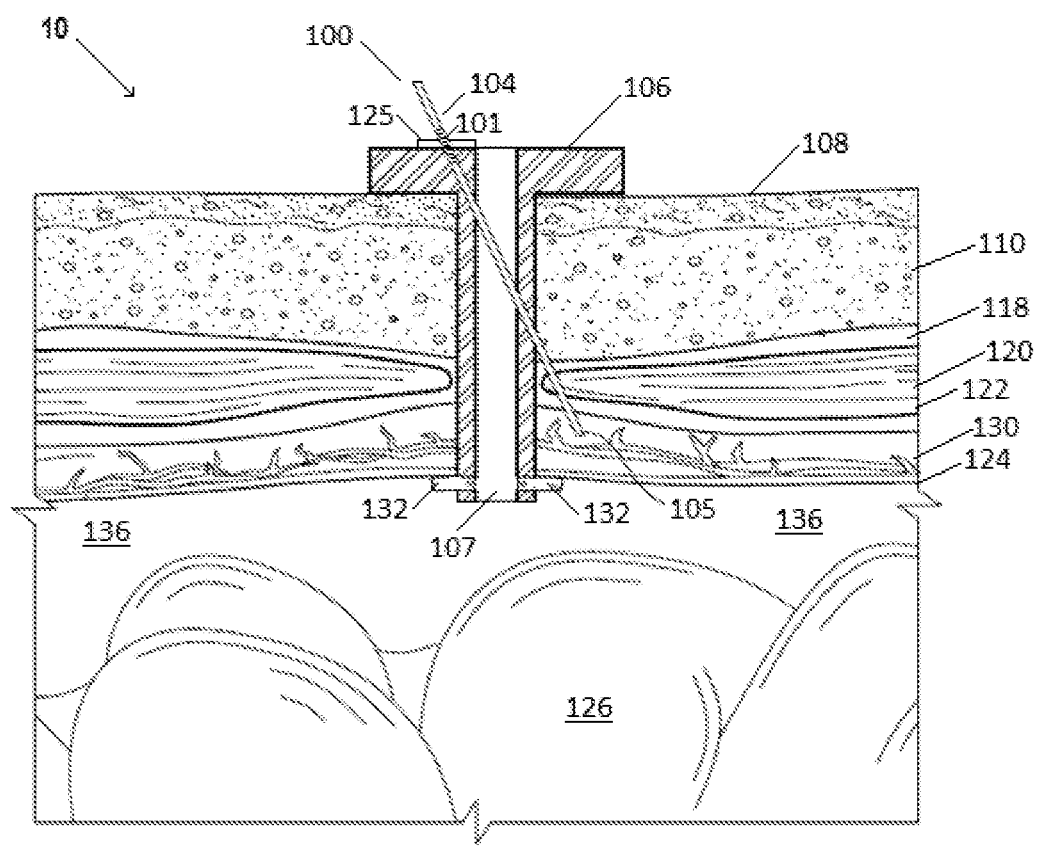
FIG. 2 shows a perspective view of another embodiment of a local anesthetic delivery device of the present disclosure and illustrates an alternative needle.

With regards to FIG. 2, another embodiment of a local anesthetic delivery device (10) is illustrated. A trocar device (106) comprising a threaded needle (103) and a distance guide controller (125) is shown. The distance guide controller (125) comprises a knob that, when turned or spun, rotatbly engages the threads (101) of the threaded needle (103) which moves the threaded needle (103) inward into the abdominal cavity (136). The threaded needle (103) comprises a distal end opening (105), and distal end opening (105) advances into the nerve plane (130) as the distance guide controller (125) is rotated. The trocar device (106) comprises at least one tubular stop tab (132), which is used to position the trocar device (106) inside the peritoneal space of the abdominal cavity (136). The at least one tubular stop tab (132) are oriented vertically or parallel to the side walls of the trocar device (106) when the trocar device (106) is inserted into the abdominal cavity (136) or coelom. Once the trocar device (106) is inserted into the peritoneal space of the abdominal cavity (106), it can be pulled upward or outward to engage the at least one tubular stop tab (132). The at least one tubular stop tab (132) is rotatably engaged with side walls of the trocar device (106) and can rotate at least 90 degrees. The at least one tubular stop stab will become oriented in a horizontal position or perpendicular to the side walls of the trocar device (106) when the trocar device (106) is pulled upward after entering the peritoneal space of the abdominal cavity (106). The at least one tubular stop tab (132) presses against the peritoneum (124) or lower abdominal wall, and the peritoneum becomes the fixed point or reference point for creating the reference plane. As a result of having the correct reference point, the distal end with openings (105) is positioned into the sensory nerve plane (130), and does not come into contact with, scrape, or puncture the intestines (126).

Figure 3:
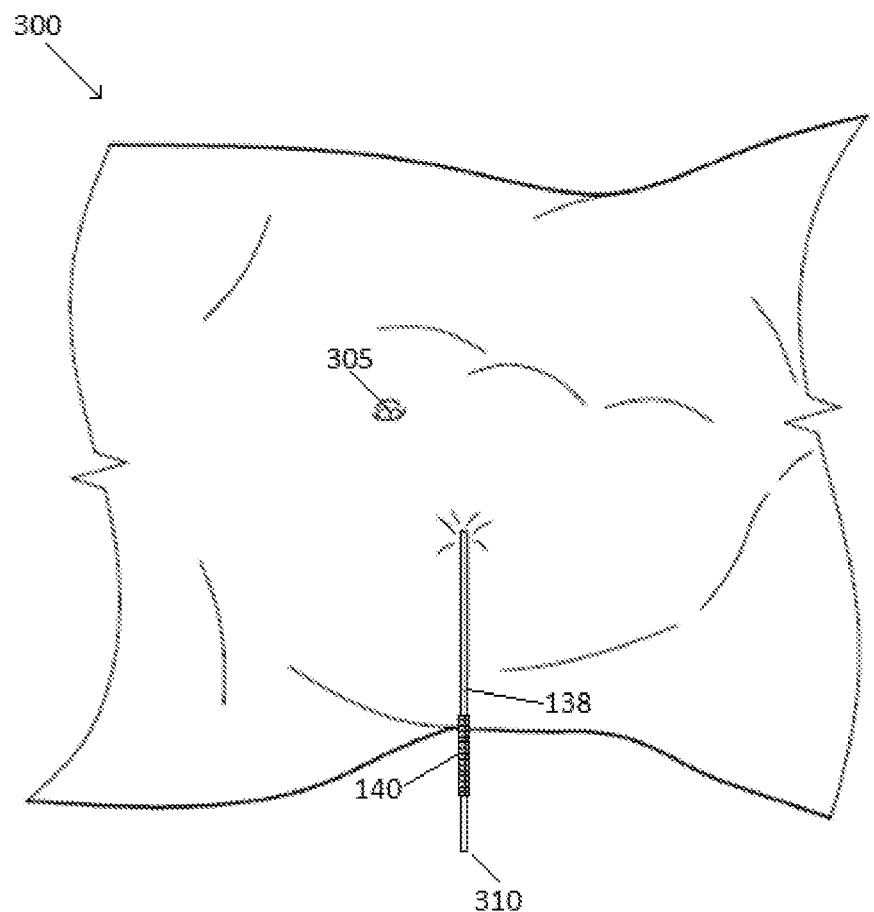
FIG. 3 shows a top view of another embodiment of a local anesthetic delivery device of the present disclosure and illustrates a specialized needle.

With respect to FIG. 3, presented is an abdominal top view (300) of one embodiment of the local anesthetic delivery device (10) illustrating a specialized needle used in RS or TAP blocks. Umbilicus 305 is illustrated without a trocar. A specialized bending tip needle (138) is shown inserted into the abdomen (300) using needlescopic methods. A grip handler (140) is used to control the functionality of the special tip needle (138) at the proximal end (310).

Figure 4:
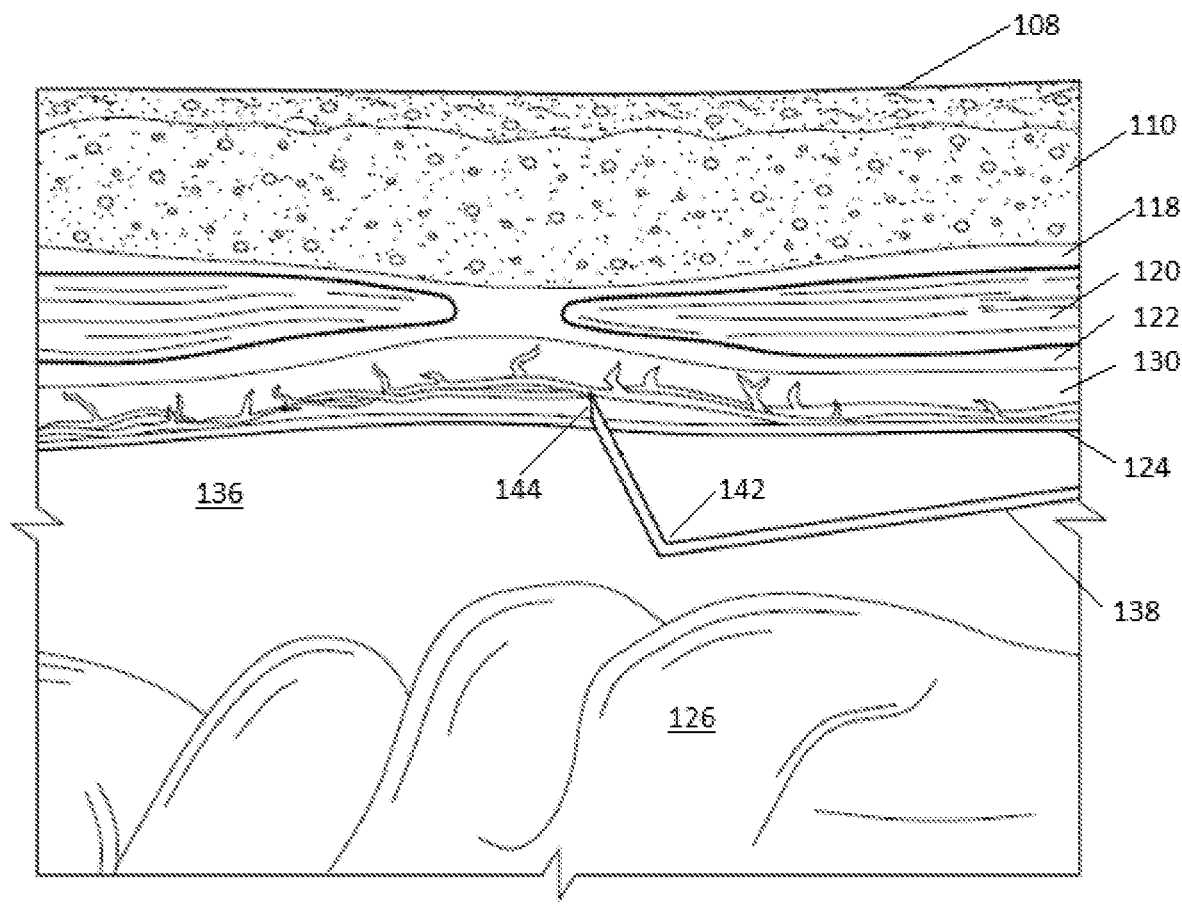
FIG. 4 shows a perspective view of another embodiment of a local anesthetic delivery device of the present disclosure and illustrates a specialized needle entering the peritoneum to reach the nerve plane.

With respect to FIG. 4, another embodiment of the local anesthetic delivery device 10 is illustrated and shows an interior cavity view of the specialized bending tip needle (138) with a bended tip (144). At least one elbow (142) of this specialized bending needle (138) permits the tip to penetrate the nerve plane (130) from the inside cavity to the target plane, where through specialized miniature openings can saturate the plane with an anesthesia. The needle tip can be a bending tip needle (138), and the bending tip needle can point upwards or outward, protecting the internal organs such as the intestines (126) from cuts. Once the specialized needle tip (144) or bending tip needle (138) traverses the peritoneum and enters the abdominal cavity (136) or intraperitoneal space, it will only travel a few more millimeters before stopping because of a physical feature designed into the needle shaft at that distance will limit how far the specialized needle tip (144) can travel into an abdominal cavity (136).

Figure 5:
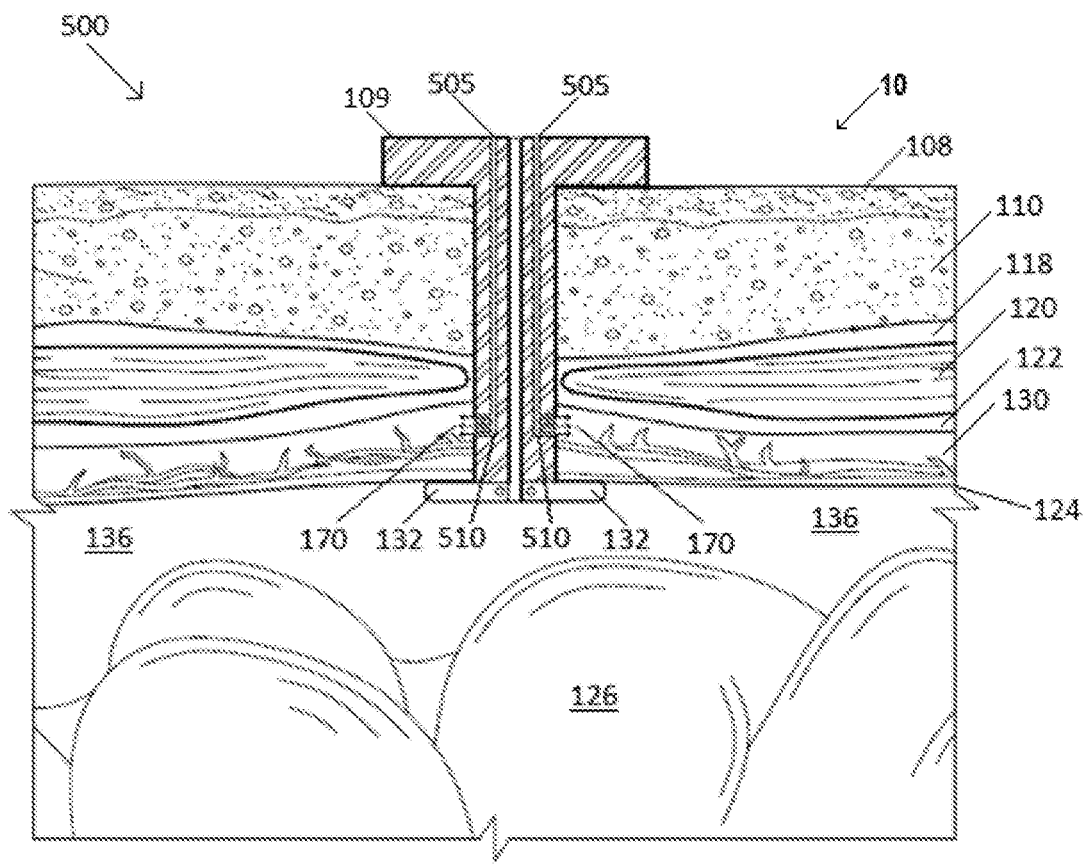
FIG. 5 shows a perspective view of another embodiment of a local anesthetic delivery device of the present disclosure and illustrates a specialized Trocar device having specialized passages that lie along the nerve plane.

With respect to FIG. 5 a perspective view of another embodiment of the local anesthetic delivery device (10) and illustrates a specialized trocar device (106) having specialized injector ports (505) and exiting ports (510) is presented used for transporting an analgesic (170) outwards from the proximal end to the distal end with multiple openings (105) to the sensory nerve plane (130). The at least one tubular stop tab (132) provide the correct reference plane (124), that allow the exiting port (510) to position the trocar analgesic exiting ports (510). No exposure to the intestines (126) takes place. A reference plane can be created with the aid of at least one tubular stop tab (132) located at the distal end of the trocar device (106).

Figure 6:
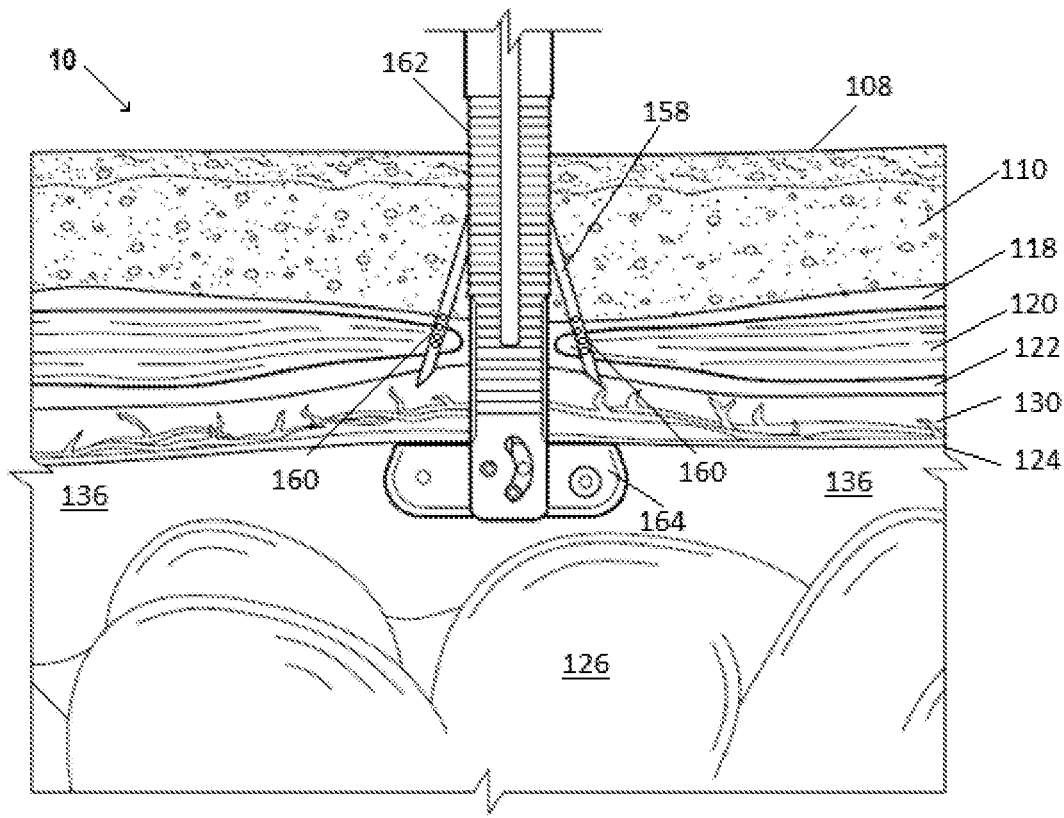
FIG. 6 shows a perspective view of another embodiment of a local anesthetic delivery device the present disclosures and illustrates a specialized anesthetic delivery device.

With respect to FIG. 6, another embodiment of the local anesthetic delivery device 10 is shown and depicts a specialized delivery device having specialized fenestrated openings (160) are used to distribute an analgesic through a predetermined range along the stylet (158). The openings can be located along the outer surface of the stylet (158). The stylet (158) is initially embedded in the elongated main body (162) and is extended by moving a lever (not shown) in the down position causing the stylet (158) to extend to a predetermined position that is in the sensory nerve plane (130). Here again, there is no exposure of the local anesthetic delivery device (10) to the intestines (126) or other internal organs.

An alternate embodiment (not shown) has a needle device with a bright LED in its center, guided to the peritoneum. Looking from the abdominal cavity (136) as the lighted source approaches the peritoneum the light source becomes brighter. Letting the surgeon know that the sensory nerve plane has been reached.

We claim:

1. A local anesthetic delivery device for delivering anesthetic to a nerve block site comprising:
   a surgical mechanism including a surgical needle having a needle body, a segment extending perpendicularly from the needle body, and a needle tip extending perpendicularly from the segment and generally parallel to the needle body;
   wherein the segment extending perpendicularly from the needle body and the needle tip are rigid and in fixed position relative to the needle body;
   wherein the needle tip is dimensioned such that when the surgical mechanism is moved so that the segment that extends perpendicularly from the needle body contacts a peritoneum of an abdominal cavity, a distal end of the needle tip is positioned at a target nerve plane so as to deliver anesthetic to the nerve block site;
   wherein the nerve block site is the transversus abdominus plane or rectus sheath.

2. The local anesthetic delivery device of claim 1, wherein a length of the needle tip corresponds to a measured distance from the peritoneum outwards to the nerve block site.

3. The local anesthetic delivery device of claim 2, wherein the distance from the peritoneum outwards to the nerve block site is 0.1 cm to 1 cm.

4. The local anesthetic delivery device of claim 1, further comprising:
   a guide controller having a knob that, when rotated, is configured to move the surgical needle in a direction parallel to the needle body to a position where the segment that extends perpendicularly from the needle body contacts the peritoneum of the abdominal cavity.

5. The local anesthetic delivery device of claim 1, wherein: a length of the needle tip corresponds to a distance from the peritoneum to the nerve block site.

6. The local anesthetic delivery device of claim 1, wherein:
   the segment extending perpendicularly from the needle body is linear; and
   wherein the needle tip is linear and extends perpendicularly from the segment and is generally parallel to the needle body.

7. The local anesthetic delivery device of claim 1, wherein:
   the needle tip is configured to pierce the peritoneum and enter the target nerve plane.

8. A local anesthetic delivery device configured for insertion into an abdominal cavity for delivering an anesthetic to a nerve block site, the device comprising:
   a surgical mechanism including a specialized surgical needle having a needle body, a segment extending perpendicularly from the needle body, and a needle tip, the segment extending from the needle body being disposed between the needle body and the needle tip and being configured such that the needle body is disposed generally parallel to the needle tip and the needle tip defining a plurality of openings; and a guide controller configured to move the specialized surgical needle along a direction parallel to the needle body as the guide controller rotates, wherein the segment extending perpendicularly from the needle body and the needle tip are rigid and in fixed position with respect to the needle body;

wherein the segment extending from the needle body is configured to contact a peritoneum of the abdominal cavity to establish a reference plane, and wherein the nerve block site being disposed a fixed distance relative to the reference plane and the openings of the needle tip being configured for distributing the anesthetic to the nerve block site;

wherein the nerve block site is the transversus abdominus plane or rectus sheath.

9. The local anesthetic delivery device of claim 8, wherein the device resists motion away from the peritoneum when the segment extending from the needle body contacts the peritoneum.

10. The local anesthetic delivery device of claim 8, wherein the distance from the peritoneum outwards to the nerve block site is 0.1 cm to 1 cm.

\* \* \* \* \*